US008236791B2

(12) United States Patent
Bresnick et al.

(10) Patent No.: US 8,236,791 B2
(45) Date of Patent: Aug. 7, 2012

(54) ASSAYS FOR S100 INHIBITORS (75) Inventors: Anne Reba Bresnick, Pelham, NY (US); Sarah Claire Garrett, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 537 days.

(21) Appl. No.: 11/989,901

(22) PCT Filed: Aug. 10, 2006

(86) PCT No.: PCT/US2006/031330
§ 371 (c)(1),
(2), (4) Date: Dec. 3, 2009

(87) PCT Pub. No.: WO2008/054354
PCT Pub. Date: May 8, 2008

(65) Prior Publication Data
US 2010/0216776 A1 Aug. 26, 2010

Related U.S. Application Data (60) Provisional application No. 60/707,393, filed on Aug. 11, 2005.

(51) Int. Cl.
A01N 43/00 (2006.01)
A01N 43/40 (2006.01)
A01N 43/36 (2006.01)
A01N 43/14 (2006.01)
A01N 43/46 (2006.01)
A61K 31/54 (2006.01)
A61K 31/497 (2006.01)
A61K 31/435 (2006.01)
A61K 31/445 (2006.01)
A61K 31/40 (2006.01)
A61K 31/38 (2006.01)
A61K 31/55 (2006.01)
C40B 30/04 (2006.01)
G01N 33/00 (2006.01)

(52) U.S. Cl. ............ 514/217; 514/225.8; 514/252.13; 514/254.07; 514/277; 514/327; 514/428; 514/437; 506/9; 436/86

(58) Field of Classification Search .............. None
See application file for complete search history.

(56) References Cited

U.S. PATENT DOCUMENTS
6,620,588 B1 9/2003 Bushman et al.
2003/0219718 A1* 11/2003 Weber et al. ............... 435/4

OTHER PUBLICATIONS

Douglass et al.,"Class-Selective Drug Detection: Fluorescently-Labeled Calmodulin as the Biorecognition Element for Phenothiazine and Tricylic Antidepressants", 2002, Bioconjugate Chemistry, 13, 1186-1192.*
Hahn et al., "A Calcium-sensitive Fluorescent Analog of Calmodulin Based on a Novel Calmodulin-binding Fluorophore", 1990, The Journal of Biological Chemistry, 265, 20335-20345.*
Vallely et al., "Solution Structure of Humans Mts1 (S100A4) As Determined by NMR Spectroscopy", 2002, Biochemistry, 41, 12670-12680.*
Garrett et al., Development of a Calcium Sensitive Mts1 (S100A4) Biosensor to Track Activation In Vivo, 2004, Abstracts of the 2004 Meeting of the American Society for Cell Biology, presentation 1518.*
Markowitz et al., Identification and Characterization of Small Molecule Inhibitors of the Calcium-Dependent S100B-p53 Tumor Suppressor Interaction, Journal of Medicinal Chemistry, 2004, pp. 5085-5093.*
Garrett et al., Development of a Calcium Sensitive Mts1 (S100A4) Biosensor to Track Activation In Vivo, Abstracts of the 2004 Meeting of the American Society for Cell Biology, presentation 1518, 2004.*
Zimmer et al., Molecular Mechanisms of S100-Target Protein Interactions, Microscopy Research and Techniques, 2003, pp. 552-559.*
The American Society for Cell Biology Presentation, Abstract publication information for the Garrett et al. reference, obatined May 8, 2011; pp. 1-2.*
Nalbant et al., entitled "Activation of Endogenous Cdc42 Visualized in Living Cells," Science, 2004, vol. 305, pp. 1615-1619.
Notification of Transmittal of the International Search Report and Written Opinion of the International Searching Authority, or the Declaration (1 page) for related application PCT/US2006/031330 with an international filing date of Aug. 10, 2006.
International Search Report (2 pages) for related application PCT/US2006/031330 with an international filing date of Aug. 10, 2006.
Written Opinion of the International Searching Authority (12 pages) for related application PCT/US2006/031330 with an international filing date of Aug. 10, 2006.
International Preliminary Report on Patentability (1 page) for related application PCT/US2006/031330 with an international filing date of Aug. 10, 2006.

* cited by examiner

*Primary Examiner* — Amber D Steele
*Assistant Examiner* — Lianko Garyu
(74) *Attorney, Agent, or Firm* — Amster, Rothstein & Ebenstein (57) ABSTRACT

Provided are methods of determining whether a compound is an inhibitor of an S100 protein. The methods utilize a biosensor that comprises the S100 protein that has a covalently bound fluorescent dye at an amino acid residue of the S100 protein that becomes less exposed to the aqueous solution upon activation of the S100 protein, where the fluorescent dye has decreased fluorescence when exposed to the aqueous solution than when protected from exposure to the aqueous solution. Also provided are methods of treating a subject having metastatic cancer.

13 Claims, 4 Drawing Sheets

ASSAYS FOR S100 INHIBITORS

CROSS-REFERENCE TO RELATED APPLICATION

This is a U.S. national phase of PCT Application No. PCT/EP2006/031330, filed Aug. 10, 2006, which claims the benefit of U.S. Provisional Application No. 60/707,393, filed Aug. 11, 2005.

STATEMENT REGARDING FEDERALLY SPONSORED RESEARCH OR DEVELOPMENT

The invention was made with government support under grant number GM069945 awarded by the National Institutes of Health. The government has certain rights in the invention.

BACKGROUND OF THE INVENTION (1) Field of the Invention

The present invention generally relates to methods of screening for protein inhibitors. More specifically, the invention is directed to methods of screening for inhibitors of S100 proteins using biosensors.

(2) Description of the Related Art

References Cited

Ambartsumian, N. S., Grigorian, M. S., Larsen, I. F., Karlstrom, O., Sidenius, N., Rygaard, J., Georgiev, G., and Lukanidin, E. (1996) Metastasis of mammary carcinomas in GRS/A hybrid mice transgenic for the mts1 gene. *Oncogene* 13, 1621-30.

Andersen, K., Nesland, J. M., Holm, R., Florenes, V. A., Fodstad, O., and Maelandsmo, G. M. (2004) Expression of S100A4 combined with reduced E-cadherin expression predicts patient outcome in malignant melanoma. *Mod Pathol* 17, 990-7.

Bhattacharya, S., Bunick, C. G., and Chazin, W. J. (2004) Target selectivity in EF-hand calcium binding proteins. *Biochim Biophys Acta* 1742, 69-79

Bjornland, K., Winberg, J. O., Odegaard, O. T., Hovig, E., Loennechen, T., Aasen, A. O., Fodstad, O., and Maelandsmo, G. M. (1999) S100A4 involvement in metastasis: deregulation of matrix metalloproteinases and tissue inhibitors of matrix metalloproteinases in osteosarcoma cells transfected with an anti-S100A4 ribozyme. *Cancer Res* 59, 4702-8.

Davies, B. R., Davies, M. P., Gibbs, F. E., Barraclough, R., and Rudland, P. S. (1993) Induction of the metastatic phenotype by transfection of a benign rat mammary epithelial cell line with the gene for p9Ka, a rat calcium-binding protein, but not with the oncogene EJ-ras-1. *Oncogene* 8, 999-1008.

Davies, M. P., Rudland, P. S., Robertson, L., Parry, E. W., Jolicoeur, P., and Barraclough, R. (1996) Expression of the calcium-binding protein S100A4 (p9Ka) in MMTV-neu transgenic mice induces metastasis of mammary tumours. *Oncogene* 13, 1631-7.

Donato, R. (2001) S100: a multigenic family of calcium-modulated proteins of the EF-hand type with intracellular and extracellular functional roles. *Int J Biochem Cell Biol* 33, 637-68.

Dulyaminova, N. G., Malashkevich, V., Almo, S. C., and Bresnick, A. R. (2005) Regulation of myosin-IIA assembly and mts1 binding by heavy chain phosphorylation. *Biochemistry* 44, 6867-86.

Ebralidze, A., Tulchinsky, E., Grigorian, M., Afanasyeva, A., Senin, V., Revazova, E., and Lukanidin, E. (1989) Isolation and characterization of a gene specifically expressed in different metastatic cells and whose deduced gene product has a high degree of homology to a Ca2+-binding protein family. *Genes Dev* 3, 1086-93.

Garrett, S. C. et al. (2004) Development of a calcium sensitive Mts1 (S100A4) biosensor to track activation in vivo. *Abstracts of the* 2004 *Meeting of the American Society for Cell Biology*, presentation 1518.

Grigorian, M., Tulchinsky, E., Zain, S., Ebralidze, A. K., Kramerov, D. A., Kriajevska, M. V., Georgiev, G. P., and Lukanidin, E. M. (1993) The mts1 gene and control of tumor metastasis. *Gene* 135, 229-238.

Grigorian, M., Ambartsumian, N., Lykkesfeldt, A. E., Bastholm, L., Elling, F., Georgiev, G., and Lukanidin, E. (1996) Effect of mts1 (S100A4) expression on the progression of human breast cancer cells. *Int J Cancer* 67, 831-41.

Gupta, S., Hussain, T., MacLennan, G. T., Fu, P., Patel, J., and Mukhtar, H. (2003) Differential expression of S100A2 and S100A4 during progression of human prostate adenocarcinoma. *J Clin Oncol* 21, 106-12.

Han, W-G. et al. (2003) *ChemPhysChem* 4, 1084-94.

Kimura, K., Endo, Y., Yonemura, Y., Heizmann, C. W., Schafer, B. W., Watanabe, Y., and Sasaki, T. (2000) Clinical significance of S100A4 and E-cadherin-related adhesion molecules in non-small cell lung cancer. *Int J Oncol* 16, 1125-31.

Lee, W. Y., Su, W. C., Lin, P. W., Guo, H. R., Chang, T. W., and Chen, H. H. (2004) Expression of S100A4 and Met: potential predictors for metastasis and survival in early-stage breast cancer. *Oncology* 66, 429-38.

Li, Z.-H., Spektor, A., Varlamova, O., and Bresnick, A. R. (2003) Mts1 regulates the assembly of nonmuscle myosin-IIA. *Biochemistry* 42, 14258-66.

Li, Z.-H., and Bresnick, A. R. (2005) The mts1 metastasis factor regulates cellular motility via a direct interaction with myosin-IIA. Submitted.

Maelandsmo, G. M., Hovig, E., Skrede, M., Engebraaten, O., Florenes, V. A., Myklebost, O., Grigorian, M., Lukanidin, E., Scanlon, K. J., and Fodstad, O. (1996) Reversal of the in vivo metastatic phenotype of human tumor cells by an anti-CAPL (mts1) ribozyme. *Cancer Res* 56, 5490-8.

Marenholz, I., Heizmann, C. W., and Fritz, G. (2004) S100 proteins in mouse and man: from evolution to function and pathology (including an update of the nomenclature). *Biochem Biophys Res Commun* 322, 1111-22.

Melan, M. A., and Sluder, G. (1992) Redistribution and differential extraction of soluble proteins in permeabilized cultured cells. Implications for immunofluorescence microscopy. *J Cell Sci* 101, 731-743.

Nikitenko, L. L., Lloyd, B. H., Rudland, P. S., Fear, S., and Barraclough, R. (2000) Localisation by in situ hybridisation of S100A4 (p9Ka) mRNA in primary human breast tumour specimens. *Int J Cancer* 86, 219-28.

Ninomiya, I., Ohta, T., Fushida, S., Endo, Y., Hashimoto, T., Yagi, M., Fujimura, T., Nishimura, G., Tani, T., Shimizu, K., Yonemura, Y., Heizmann, C. W., Schafer, B. W., Sasaki, T., and Miwa, K. (2001) Increased expression of S100A4 and its prognostic significance in esophageal squamous cell carcinoma. *Int J Oncol* 18, 715-20.

Okada, H., Danoff, T. M., Kalluri, R., and Neilson, E. G. (1997) Early role of Fsp1 in epithelial-mesenchymal transformation. *Am J Physiol* 273, F563-74.

Palmer. A. E. et al. (2004) *Proc. Natl. Acad. Sci. USA* 101, 17404-9.

Platt-Higgins, A. M., Renshaw, C. A., West, C. R., Winstanley, J. H., De Silva Rudland, S., Barraclough, R., and Rudland, P. S. (2000) Comparison of the metastasis-inducing protein S100A4 (p9ka) with other prognostic markers in human breast cancer. *Int J Cancer* 89, 198-208.

Ravasi, T., Hsu, K., Goyette, J., Schroder, K., Yang, Z., Rahimi, F., Miranda, L. P., Alewood, P. F., Hume, D. A., and Geczy, C. (2004) Probing the S100 protein family through genomic and functional analysis. *Genomics* 84, 10-22.

Rety, S., Sopkova, J., Renouard, M., Osterloh, D., Gerke, V., Tabaries, S., Russo-Marie, F., and Lewit-Bentley, A. (1999) The crystal structure of a complex of p11 with the annexin II N-terminal peptide. *Nat Struct Biol* 6, 89-95.

Rudland, P. S., Platt-Higgins, A., Renshaw, C., West, C. R., Winstanley, J. H., Robertson, L., and Barraclough, R. (2000) Prognostic significance of the metastasis-inducing protein S 100A4 (p9Ka) in human breast cancer. *Cancer Res* 60, 1595-603.

Rustandi, R. R., Baldisseri, D. M., Drohat, A. C., and Weber, D. J. (1999) Structural changes in the C-terminus of Ca2+-bound rat S100B (beta beta) upon binding to a peptide derived from the C-terminal regulatory domain of p53. *Protein Sci* 8, 1743-51.

Saleem, M., Adhami, V. M., Ahmad, N., Gupta, S., and Mukhtar, H. (2005) Prognostic significance of metastasis-associated protein S100A4 (Mts1) in prostate cancer progression and chemoprevention regimens in an autochthonous mouse model. *Clin Cancer Res* 11, 147-53.

Takenaga, K., Nakamura, Y., Endo, H., and Sakiyama, S. (1994a) Involvement of S100-related calcium-binding protein pEL98 (or mts1) in cell motility and tumor cell invasion. *Jpn J Cancer Res* 85, 831-9.

Takenaga, K., Nakamura, Y., and Sakiyama, S. (1994) Expression of a calcium binding protein pEL98 (mts1) during differentiation of human promyelocytic leukemia HL-60 cells. *Biochem Biophys Res Commun* 202, 94-101.

Takenaga, K., Nakamura, Y., and Sakiyama, S. (1997) Expression of antisense RNA to S100A4 gene encoding an S100-related calcium-binding protein suppresses metastatic potential of high-metastatic Lewis lung carcinoma cells. *Oncogene* 14, 331-7.

Toutchkine, A., Kraynov, V., and Hahn, K. (2003) Solvent-sensitive dyes to report protein conformational changes in living cells. *J Am Chem Soc* 125, 4132-45.

Vallely, K. M., Rustandi, R. R., Ellis, K. C., Varlamova, O., Bresnick, A. R., and Weber, D. J. (2002) Solution structure of human mts1 (S100A4) as determined by NMR spectroscopy. *Biochemistry* 41, 12670-80.

Wang, Y. et al. (2005) *Nature* 434, 1040-5.

Yonemura, Y., Endou, Y., Kimura, K., Fushida, S., Bandou, E., Taniguchi, K., Kinoshita, K., Ninomiya, I., Sugiyama, K., Heizmann, C. W., Schafer, B. W., and Sasaki, T. (2000) Inverse expression of S100A4 and E-cadherin is associated with metastatic potential in gastric cancer. *Clin Cancer Res* 6, 4234-42.

Zimmer, D. B., Wright Sadosky, P., and Weber, D. J. (2003) Molecular mechanisms of S100-target protein interactions. *Microsc Res Tech* 60, 552-9.

U.S. Pat. No. 6,197,928.

At present there are 21 known human S100 family members, which generally form homodimers with total molecular masses ranging from 20-24 kDa. For example, Mts1, which is also known as S100A4, is a member of the S100 family of calcium-binding proteins that is directly involved in tumor metastasis. The S100 proteins contain a conserved C-terminal EF hand that has a high affinity for calcium, and an N-terminal noncanonical EF that binds calcium with low affinity (Marenholz et al., 2004). In addition, many of the S100 family members are expressed in a highly tissue-specific manner (Ravasi et al., 2004). The S100 proteins have been implicated in the calcium-dependent regulation of a broad range of intracellular activities including substrate phosphorylation, the assembly/disassembly of cytoskeletal proteins, the modulation of enzyme activity, the regulation of cell cycle events and calcium homeostasis (Donato, 2001). Importantly, most S100 family members display a high degree of target specificity, suggesting that individual S100 proteins regulate specific cellular processes. Despite the significant number of S100 family members in vertebrates, they are absent from the genomes of invertebrates (Marenholz et al., 2004; Ravesi et al., 2004). Interestingly, alterations in S100 function are associated with a number of human diseases (Zimmer et al., 2003), including for example cancer (S100s A2, A3, A4, A5, A6, A10, P and B), inflammatory diseases (S100s A8, A9 and A12) cardiomyopathies (S100A1), psoriasis (S100A7, S100A7L1/A15) and neurodegeneration (S100B). Thus, S100 proteins are important diagnostic markers as well as therapeutic targets for many diseases.

The role of S100A4 in cancer has been most widely examined in mammary tumor cells and animal models of breast cancer, which have demonstrated that S100A4 exhibits a strong causal link with breast cancer metastasis. Metastatic rat and mouse mammary tumor cells contain elevated levels of S100A4 as compared to nonmetastatic cells (Ebralidze et al., 1989). Similarly, S100A4 expression is higher in malignant human breast tumors than in benign tumors (Nikitenko et al., 2000) and correlates strongly with poor patient survival (Platt-Higgins et al., 2000; Rudland et al., 2000; Lee et al., 2004). Overexpression of S100A4 in nonmetastatic rat (Davies et al., 1993) and mouse (Grigorian et al., 1996) mammary tumor cells confers a metastatic phenotype, whereas in metastatic cells, a reduction in S100A4 expression suppresses metastatic potential (Takenaga et al., 1997; Maelandsmo et al., 1996). Transgenic mice that overexpress S100A4 in the mammary epithelium are phenotypically indistinguishable from wild-type mice (Ambartsumian et al., 1996), demonstrating that S100A4 itself is not tumorigenic; however, transgenic mouse models of breast cancer have shown that S100A4 expression correlates with metastasis. MMTV-neu and GRS/A animals are characterized by a high incidence of mammary tumors that rarely metastasize; overexpression of S100A4 in the mammary epithelium of these animals causes more invasive primary tumors and the appearance of metastases in the lungs (Ambartsumian et al., 1996; Davies et al., 1996). In addition to breast cancer, S100A4 has been shown to be a prognostic marker in a number of human cancers, including esophageal-squamous cancers (Ninomiya, 2001), non-small lung cancers (Kimura et al., 2000), primary gastric cancers (Yonemura et al., 2000), malignant melanomas (Andersen et al., 2004) and prostate cancers (Gupta et al., 2003; Saleem et al., 2005).

S100A4 expression levels correlate strongly with cell motility. S100A4 is expressed at elevated levels in macrophages, lymphocytes and neutrophils, all highly motile cells (Grigorian et al., 1993). In addition, fibroblasts and epithelial tumor cells that overexpress S100A4 display increased migratory properties (Takenaga et al., 1994a). S100A4 is also expressed during epithelial-mesenchymal transformations, and in particular, is associated with mesenchymal cell morphology and motility (Okada et al., 1997). Lastly, S100A4 expression is induced during macrophagic or granulocytic differentiation of human promyelocytic leukemia cells and is coincident with increased motility (Takenaga et al., 1994b). Conversely, ablation or reduction of S100A4 expression correlates with decreased cellular motility (Takenaga et al., 1997; Bjornland et al., 1999). These observations suggest that S100A4 may promote a metastatic phenotype through the regulation of cellular motility.

S100A4 preferentially binds to nonmuscle myosin-IIA and promotes the monomeric, unassembled state (Li et al., 2003). The S100A4 binding site maps to residues 1909-1924 in the C-terminal end of the coiled-coil of the myosin-IIA heavy chain and phosphorylation by casein kinase 2 on Ser1944 inhibits S100A4 binding (Dulyaminova et al., 2005). Moreover, S100A4 regulates the protrusive activity of migrating tumor cells via a direct and specific interaction with myosin-IIA (Li and Bresnick, 2005). These observations support a model in which S100A4 modulates cellular motility and metastasis via regulation of myosin-IIA.

In addition to these biochemical and cellular studies, a detailed atomic structure of the human apo-S100A4 has also been determined (Vallely et al., 2002).

There are no known inhibitors of S100 proteins. Since S100 proteins are important in disease, there is a need for methods to screen for inhibitors of S100 proteins. The present invention addresses this need.

SUMMARY OF THE INVENTION

Accordingly, the inventors have developed rapid and simple methods of identifying inhibitors of S100 proteins. These methods allow for high throughput screening for such inhibitors.

Thus, the invention is directed to methods of determining whether a compound is an inhibitor of an S100 protein. The methods comprise combining the compound with $Ca^{+2}$ and a biosensor of the S100 protein in an aqueous solution, where the biosensor comprises the S100 protein that has a covalently bound fluorescent dye at an amino acid residue of the S100 protein, where the local environment around the amino acid residue changes with a conformational change in the S100 protein upon the binding of $Ca^{+2}$ to the S100 protein, and where the fluorescent dye has increased fluorescence when the S100 protein binds $Ca^{+2}$. In these embodiments, the compound is an inhibitor of the S100 protein if it prevents increased fluorescence upon exposure of the biosensor to $Ca^{+2}$.

The invention is also directed to methods of treating a subject having a metastatic cancer,. The methods comprise administering a compound that inhibits an S100A4 to the subject in a manner sufficient to inhibit the S100A4, wherein the compound is flupenthixol-cis, fluphenazine, perphenazine, prochlorperazine, trifluoperazine, chlorprothixene, cyproheptadine, clomipramine, bepridil, ketoconazole, or loperamine.

The invention is additionally directed to methods of treating a subject having a metastatic cancer. The methods comprise (a) identifying an inhibitor of S100A4 using the above-described biosensor method, then (b) administering the S100A4 inhibitor to the subject in a manner sufficient to inhibit an S100A4 in the subject.

DETAILED DESCRIPTION OF THE INVENTION

The inventors have developed rapid and simple methods for screening for inhibitors of S100 proteins.

Thus, in some embodiments, the invention is directed to methods of determining whether a compound is an inhibitor of an S100 protein. The methods comprise combining the compound with $Ca^{+2}$ and a biosensor of the S100 protein in an aqueous solution, where the biosensor comprises the S100 protein that has a covalently bound fluorescent dye at an amino acid residue of the S100 protein, where the local environment around the amino acid residue changes with a conformational change in the S100 protein upon the binding of $Ca^{+2}$ to the S100 protein, and where the fluorescent dye has increased fluorescence when the S100 protein binds $Ca^{+2}$. In these embodiments, the compound is an inhibitor of the S100 protein if it prevents increased fluorescence upon exposure of the biosensor to $Ca^{+2}$.

Without being bound to any particular mechanism for the biosensor response, it is believed that $Ca^{+2}$ binding to the S100 protein changes the effective local polarity around the amino acid residue that has the fluorescent dye, where the fluorescence of the dye is sensitive to to solvent accessibility, hydrogen binding and other local interactions.

These methods are useful for determining whether any compound is an inhibitor of any S100 protein. Nonlimiting examples of such proteins include S100A1, S100A2, S100A3, S100A4, S100A5, S100A6, S100A7, S100A7L2, S100A7L3, S100A7L4, S100A8, S100A9, S100A10, S100A11, S100A12, S100A13, S100A14, S100A15, S100A16, S100B, S100P, S100Z and CALB3. The S100 protein can also be from any species, including humans. In some preferred embodiments, the S100 protein is S100A4.

Any dye that has decreased fluorescence when exposed to increases in local polarity can be used in these methods. Preferably, the dye is a merocyanine dye, since those dyes are the best characterized of dyes with the desired characteristics. A preferred example of a merocyanine dye is ISO-IAA, as utilized in the Example. See also Hahn et al., 2003; Toutchkine et al., 2003.

In these embodiments, the dye can be covalently bound to any amino acid residue of the S100 protein that becomes less exposed to the aqueous solution upon activation of the S100 protein. The skilled artisan could identify several such residues without undue experimentation. A preferred example of such a residue is an amino acid residue that is at a three-dimensional position equivalent to Cys81 of S100A4. Such a residue could be easily identified for any S100 protein from any species.

In some embodiments, the fluorescence of the biosensor is measured in a control sample (with $Ca^{+2}$) without the compound, and compared with the fluorescence of the biosensor in the presence of the compound. Alternatively, the fluorescence of the biosensor can be measured in the presence of the compound both before and after adding $Ca^{+2}$. In these embodiments, when the compound is an inhibitor of the S100, adding $Ca^{+2}$ will cause less of a difference in fluorescence intensity than when $Ca^{+2}$ is added in the absence of the compound.

When a compound is identified that inhibits the S100, its action can be further characterized. For example, the compound can be evaluated to determine whether it inhibits calcium binding to the S100 protein, or whether it inhibits the interaction of the S100 protein with a target of the S100 protein. Such evaluations can be made by the skilled artisan without undue experimentation using known methods.

The instant methods can be easily adapted for screening more than one compound. Thus, the methods further comprise determining whether a second compound is an inhibitor of an S100 protein. Preferably, the compound is part of a chemical library, wherein at least 10 compounds of the chemical library are tested for the ability to inhibit an S100 protein. More preferably, at least 50 compounds of the chemical library are tested for the ability to inhibit an S100 protein. In the most preferred embodiments, at least 100 compounds of the chemical library are tested for the ability to inhibit an S100 protein. The skilled artisan would understand that the invention methods can also be adapted for high throughput screening of chemical libraries for S100 inhibitors.

These methods can be utilized in efforts to modify a known S100 inhibitor to improve its characteristics such as solubility, side effects or S100 inhibitory specificity. Preferably, the modification changes less than half of the known S100 inhibitor, by weight. More preferably, the modification changes one moiety of the known S100 inhibitor. The known S100 inhibitor can be an inhibitor of any S100 protein, such as an S100A4 inhibitor. Examples of S100A4 inhibitors that can be modified then tested using the invention methods are flupenthixol-cis, fluphenazine, perphenazine, prochlorperazine, trifluoperazine, chlorprothixene, cyproheptadine, clomipramine, bepridil, ketoconazole and loperamine (See Example 2).

Compounds that are identified as S100 inhibitors using the invention biosensor can be used for therapeutic treatment of any disease or disorder where inhibition of the S100 would benefit the patient. An example is the use of S100A4 inhibitors to inhibit metastasis in cancer. See Example 2.

Thus, the invention is additionally directed to methods of treating a metastatic cancer in a subject. The methods comprise administering a compound to the subject in an amount effective to treat the metastatic cancer. In these methods, the compound is flupenthixol-cis, fluphenazine, perphenazine, prochlorperazine, trifluoperazine, chlorprothixene, cyproheptadine, clomipramine, bepridil, ketoconazole, or loperamine.

These methods are useful for treating any form of metastatic cancer including breast cancer, bladder cancer, gallbladder cancer, esophageal cancer, non-small lung cancer, gastric cancer, melanoma, prostate cancer, pancreatic cancer, thyroid cancer, or hepatocellular cancer.

The invention is further directed to methods of treating a subject having a metastatic cancer. These methods comprise (a) identifying an inhibitor of S100A4 using the above-described screening method, then (b) administering the S100A4 inhibitor to the subject in a manner sufficient to inhibit S100A4 in the subject. These methods are useful for treating a subject having any form of metastatic cancer including breast cancer, bladder cancer, gallbladder cancer, esophageal cancer, non-small lung cancer, gastric cancer, melanoma, prostate cancer, pancreatic cancer, thyroid cancer, or hepatocellular cancer.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

An S100A4 Biosensor

Figure 1:
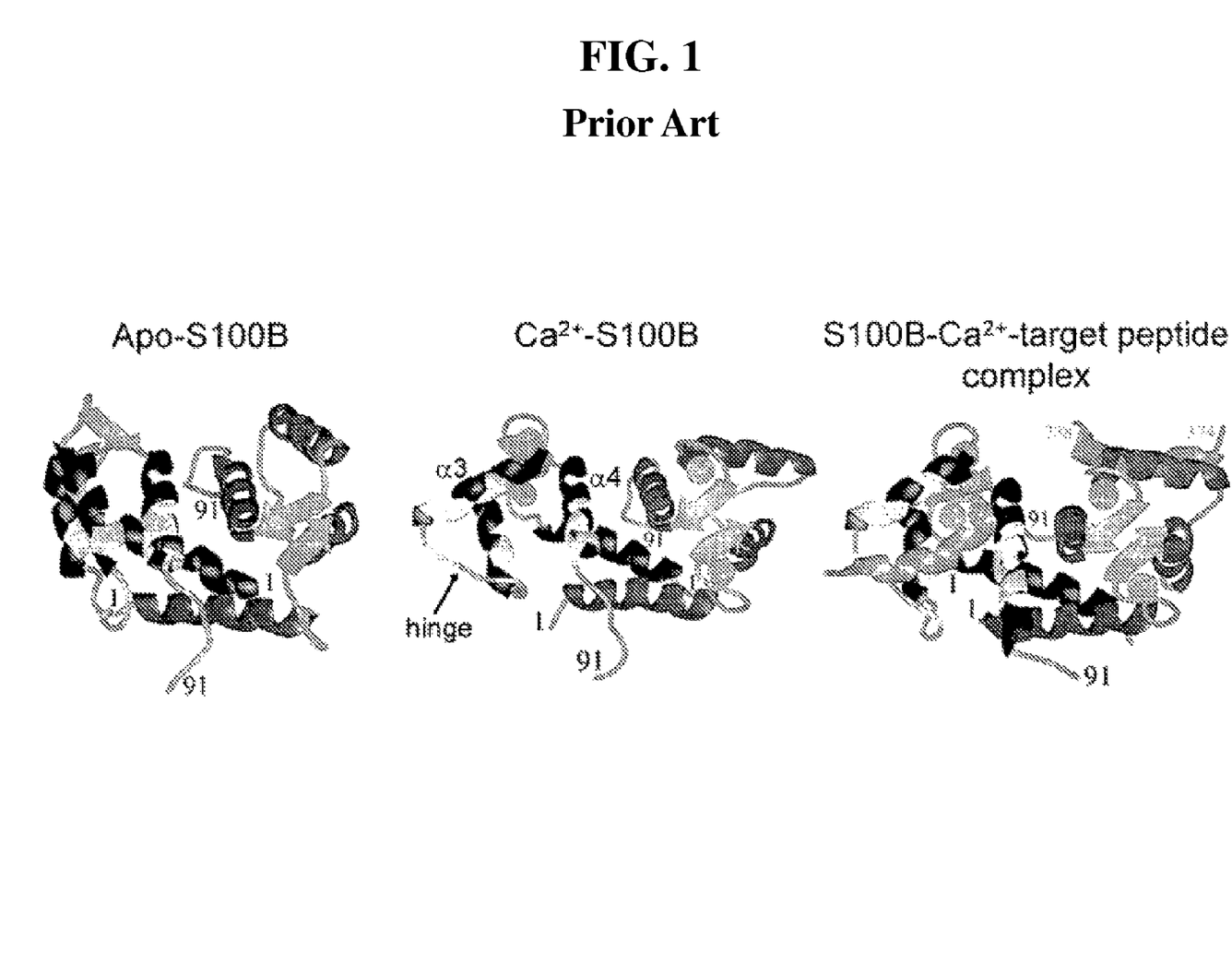
FIG. 1 is prior art illustrations showing ribbon structures of S100B. Upon calcium addition (spheres), there is a large conformational change between helices 3 and 4 that exposes a hydrophobic cleft. Two peptides bind per S100B dimer, but for clarity residues on only one monomer are shown.

The S100 proteins are symmetric dimers in which each monomer contains N- and C-terminal EF-hands connected by a loop or hinge region. As shown in FIG. 1 for S100B, calcium-binding to the C-terminal EF-hand induces a significant change in the interhelical angle between helices 3 and 4 ($\alpha 3$ and $\alpha 4$) that flank the calcium-binding loop, which exposes a hydrophobic cleft that constitutes the calcium-dependent binding surface for target molecules (FIG. 1) (Rety et al., 1999; Rustandi et al., 1999). The calcium-induced conformational change that is observed with the S100 family members and the exposure of a hydrophobic target binding cleft makes the S100 proteins ideal candidates for the creation of fluorescent biosensors using the merocyanine dyes developed by Klaus Hahn (Toutchkine et al., 2003). These fluorochromes display sensitivity to solvent polarity and hydrogen bonding, and thus respond to changes in the hydrophobicity of their protein environment. Since our full complement of S100A4 structures are not complete, we utilized a structure-based alignment of S100B and S100A4 to identify appropriate residues for mutagenesis and dye attachment.

Figure 2:
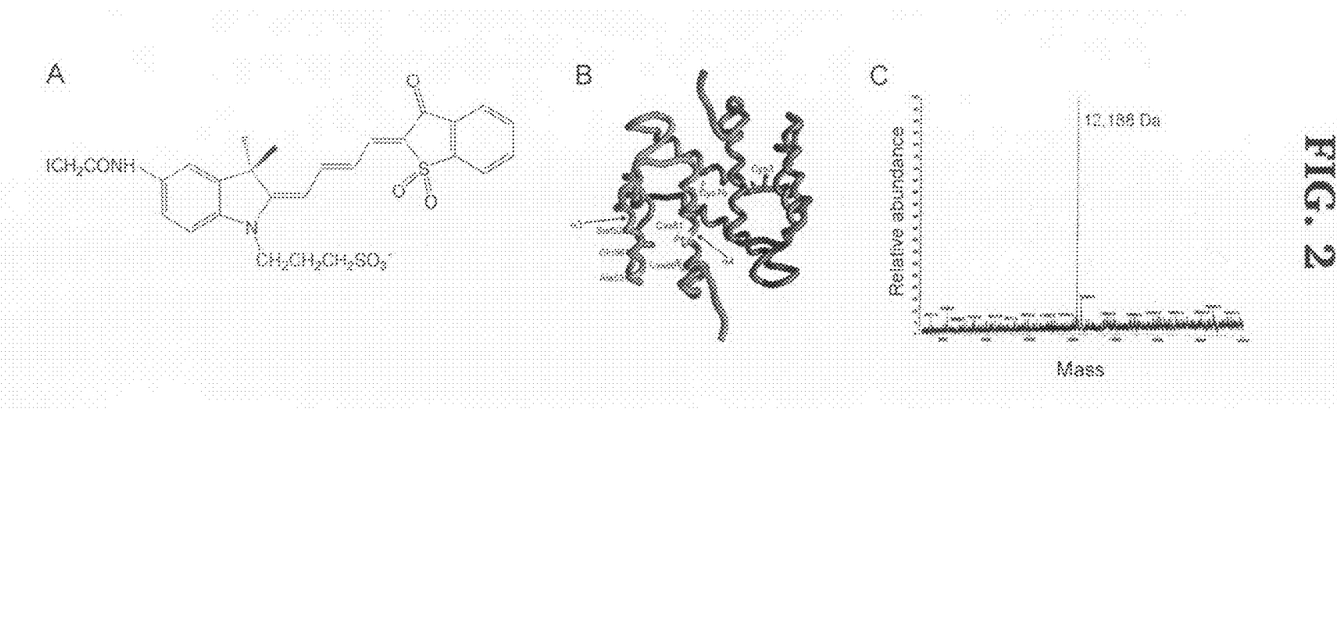
FIG. 2 is a chemical structure, an NMR structure, and a mass spectrum showing labeling of the human S100A4 with the merocyanine dye. Panel A shows the chemical structure of the ISO-IAA merocyanine dye used to create the Mero-S100A4 biosensor described in the example. Panel B shows the NMR structure of the human apo-S100A4. The two monomers comprising the S100A4 dimer are depicted with the positions of the cysteines indicated on one monomer. Panel C shows a mass spectrum of the Mero-S100A4. A major peak with a mass of 12,188 Da was detected, which corresponds to the mass of an S100A4 monomer with a single dye attached (mass of unlabeled monomer=11,634.5 Da).

We produced and characterized a fluorescent analog of S100A4 (Mero-S100A4) that reports calcium binding, and thus serves to identify activated S100A4 (Garrett et al., 2004). To produce the S100A4 biosensor that monitors protein activation (i.e., calcium binding) Cys81 was derivatized with the ISO-IAA dye to a stoichiometry of 1:1 (FIG. 2).

Figure 3:
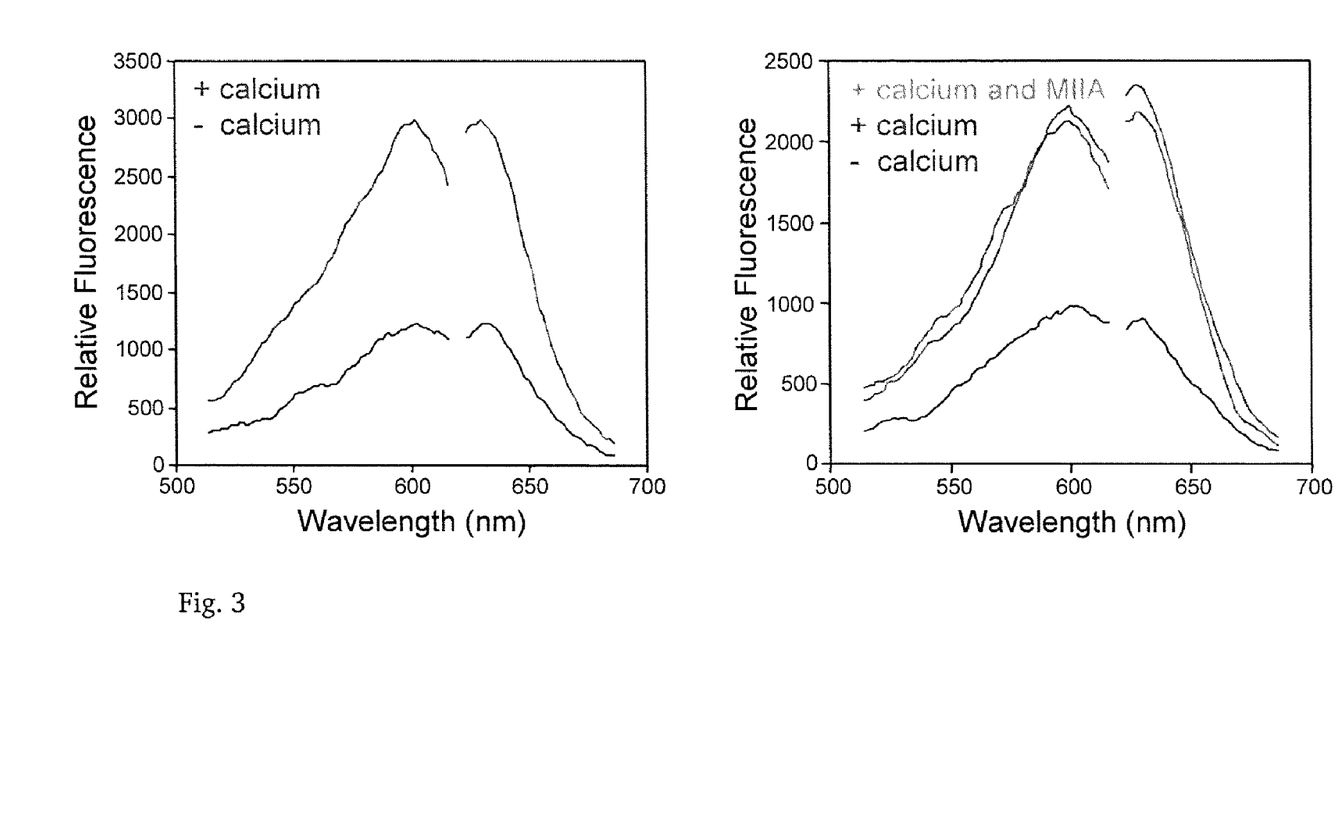
FIG. 3 is graphs of experimental results showing fluorescence spectra of the Mero-S100A4 biosensor. The left panel shows the excitation and emission spectra of Mero-S100A4 in the absence (lower spectrum) or presence (upper spectrum) of calcium. The right panel shows the same spectra as the left hand panel and also excitation and emission spectra of Mero-S100A4 upon binding myosin-IIA (uppermost spectrum).
Figure 4:
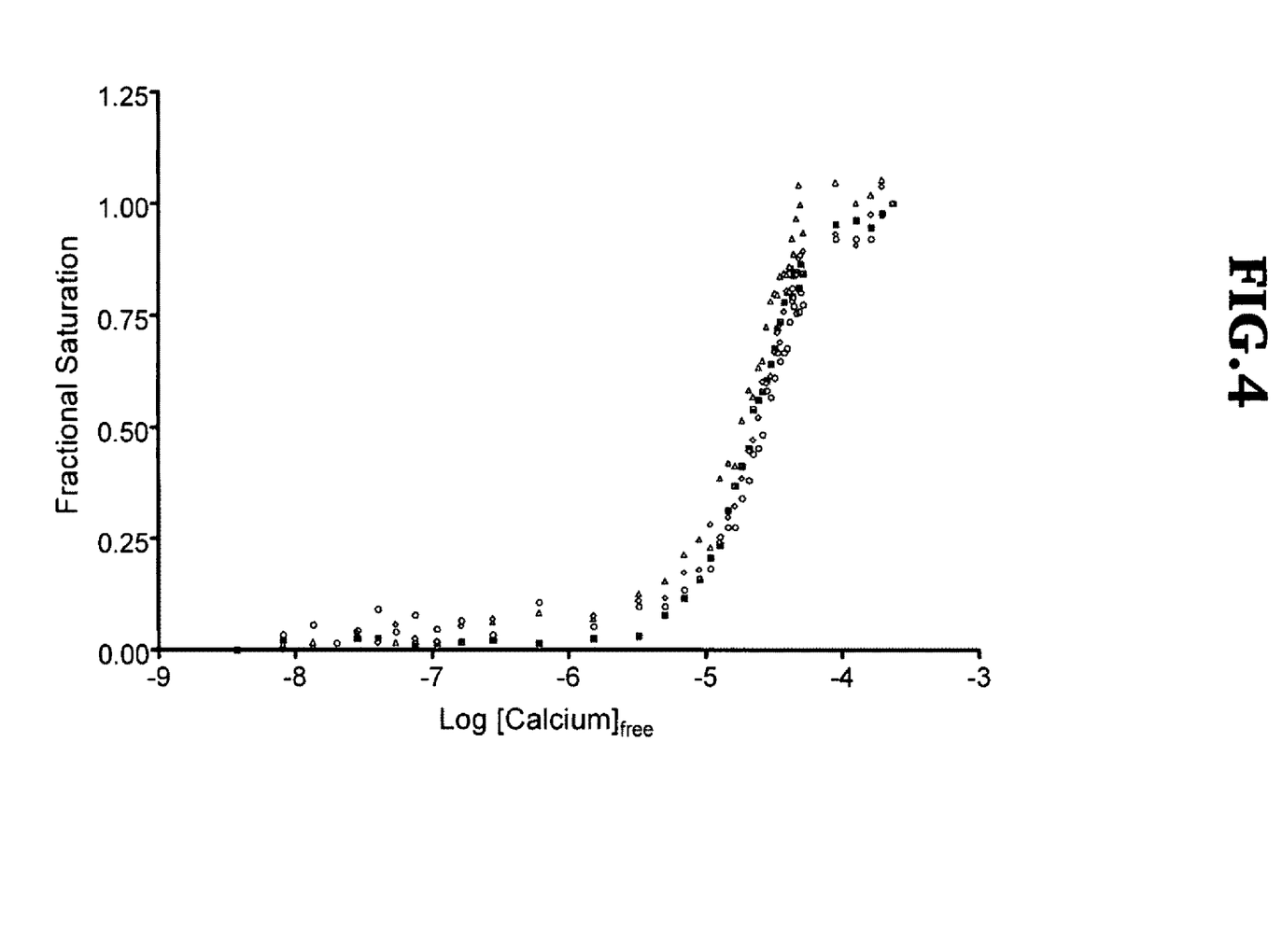
FIG. 4 is a graph of experimental results showing calcium titration of the Mero-S100A4 biosensor.

The Mero-S100A4 displays a 2.8-fold increase in fluorescence intensity at 634 nm in the presence of calcium relative to the biosensor in the absence of calcium (FIG. 3, left panel). Binding of the Mero-S100A4 to myosin-IIA results in only a small increase in fluorescence intensity (FIG. 3, right panel). These observations indicate that the S100A4 biosensor reports only calcium binding and not target binding. In addition, calcium binding studies indicate that mutagenesis and dye attachment have not altered the binding affinity of the labeled S100A4 for calcium (data not shown). Calcium titration experiments in the absence of myosin-IIA demonstrate that Mero-S100A4 displays a transition in the low micromolar range (FIG. 4), demonstrating that the biosensor is capable of reporting physiological calcium concentrations.

A previously described EF hand biosensor is a genetically encoded biosensor that utilizes green fluorescent protein (GFP) variants fused to calmodulin and calmodulin binding peptides (U.S. Pat. No. 6,197,928; Palmer et al., 2004; Wang et al., 2005). Calcium binding is measured by fluorescent resonance energy transfer (FRET) between the two GFP variants. The biosensor described herein is not genetically encoded—the biosensor is created by covalently labeling purified S100A4 with the merocyanine dye, which is chemically synthesized. In addition, the biosensor described here does not use FRET to monitor calcium binding, rather binding is detected due to a conformational change that occurs in S100A4 upon calcium binding. Since the quantum yield of the merocyanine dye is dependent on solvent polarity and hydrogen bonding, this enables the dye to report changes in its protein environment that occur due to conformational changes. It should be noted that FRET-based biosensors typically demonstrate a ~1.8-fold increase in fluorescence intensity, whereas the S100A4 biosensor displays a 2.8-fold increase in fluorescence intensity. Thus the S100A4 biosensor is a brighter biosensor, which can be more readily detected in vivo or in vitro. The biosensor described herewith is therefore much better adapted for use in inhibitor screening assays than the previously described biosensor.

EXAMPLE 2

Screening for S100A4 Inhibitors using an S100A4 Biosensor

A total of 333 FDA approved drugs were tested for their ability to inhibit S100A4, using the biosensor described in Example 1. Screening assays used 5 μM S100A4 biosensor (dimer concentration), 100 μM FDA approved drug, buffer: 50 mM Tris-HCl, pH 7.5, 150 mM NaCl, 0.3 mM $CaCl_2$, 0.02% $NaN_3$, 1 mM DTT, 10% DMSO. Assays with EGTA had a final concentration of 2 mM EGTA. 100 μl assay volume. Compounds that showed S100A4 inhibitor activity were further subjected to the biosensor assay to determine the $IC_{50}$ value using 5 μM S100A4 biosensor, 0-400 μM small molecule inhibitor, and the buffer as above.

The compounds tested were acemtacin, acetamido(4-)phenol, acetohexamide, acetylsalicyclic acid, acycloguanosine, warfarin, allopurinol, alverine, althiazide, amantadine, amiloride, aminoglutethimide, amoxapine, aniracetam, antazoline, antipyrine, thioguanine, apomorphine hydrochloride, astemizole, atenolol, atropine, azlocilin, bendroflumethiazide, benzthiazide, bepridil, betahistine, betamethasone, bezafibrate, bretylium tosylate, budesonide, bumetanide, bupropion, busulfan, biphenylacetic acid, canrenoic acid, captopril, cefaclor, cefadroxil, chloramphenicol, chlormezanone, chloroquine, chlorpheniramine, ciclopirox olamine, cinnarizine, cinoxacin, cis-platinum(II) diamine, clemastine, clotrimazole, colchicine, cyproheptadine, cyclizine, chlorpropamide, clomipramine, clozapine, debrisoquine, sulfate, deprenyl hydrochloride, floxuridine, diazoxide, diclofenac, dicyclomine, diethylstilbestrol, diflunisal, digitoxin, digoxin, dihydroergotamine, dimenhydrinate, dimethyl(1,1)biguanide, diphenhydramine, DOPA (cloudy or brown), disopyramide, phenyloin, doxepine, doxylamine, domperidone, econazole, erythromycin, eserine, ethacrynic acid, ethambutol, ethyl p-aminobenzoate, etoposide, mestranol, estradiol, famotidine, fenbufen, fenofibrate, fenoprofen, fenoterol, flavoxate, fluconazole, flunisolide, fluoro(5-)uracil, flupenthixol-cis, fluphenazine, flurbiprofen, flutamide, furosemide, flucytosine, gemfibrozil, guanethidine, haloperidol, hexamethylenetetramine, hydralazine, hydrochlorothiazide, hydrocortisone, hydroflumethiazide, hydroxyzinc, ibuprofen, imipramine, indapamide, indomethicin, ipratropium bromide, isonicotinic acid hydrazide, isosorbide dinitrate, kanamycin sulfate, ketoprofen, ketotifen, ketoconazole, isoproterenol-(-), labetalol, lidocaine, lithium carbonate, loperamide, magnesium sulfate, mannitol-(D), maprotiline, meclofenamic acid, mefenamic acid, acetoxy(17 alpha)-6-methyl-4,6-pregnadiene-3,20-dione, metaproterenol, metoclopramide, metolazone, metoprolol, metricane, melphalan, mercapto(6-)purine, methyl(6alpha)-17-alpha-hydroxyprogesterone, medrol, miconazole, minoxidil, mitoxantrone, nabumetone, nadolol, naphazoline hydrochloride, naproxen, nefopam, neomycin sulfate, (-)-nicotine, nimodipine, nitrendipine, nitrofurantoin, nortriptyline, oxybutynin chloride, oxymetazoline hydrochloride, oxytetracycline, penicillin G, phenelzinc, pheniramine, phenoxymethyl penicillinic acid, phentolamine hydrochloride, phenyl(trans-2)cyclopropylamine, phenylbutazone, phenylephrine hydrochloride-(L), piracetam, prazosin, prednisolone, primaquine, probenecid, procainamide, propantheline bromide, propyl (2-) pentanoic acid sodium salt, propyl(3-)xanthine, promethazine, protriptyline, pyrazinamide, pyrilamine, pyrimethamine, quinidine, quinine, ranitidine, naloxone, nicardipine, nicergoline, nifedipine, norfloxacin, novobiocin, ofloxacin, orphenadrine, oxacillin, penicillamine-(D), penicillamine-(L), perphanazine, phenindione, phenoxybenzamine, phosphomycin, pimozide, pindolol, piperacillin sodium salt, piroxicam, prochlorperazine, procyclidine, promazine, propafenone, propericyazine, propranolol, rescinnamine, ribavirin, streptomycin sulfate, sulfabenzamide, sulfamethizole, sulpriride, tamoxifen citrate, terfenadine, thiothixene, tobramycin sulfate, tolnaftate, trimethoprim, trimipramine, tripolidine, tulobuterol, vancomycin, diltiazem, milrinone, cyclosporin A, aclarubicin, pargyline, noscapine hydrochloride, 2-chorodeoxyadenosine, clindamycin, fluoro(2)adenine 9-beta-D-arabinofuranoside, netilmicin, doxorubicin, oxiracetam, trifluoperazine, oxprenolol, methy (alpha)IDOPA, paclitaxel, etodolac, curcumin, ketanserin tartrate, cephalexin, lovastatin, cyclophosphamide, nafcillin, azathioprine, capreomycin, carmustine, chlortetracycline, cycloserine-(D), cycloserine-(L), demeclocycline, diphenylpyraline, dipyridamole, etidronic acid disodium salt, griseofulvin, guanabenz acetate, L-3,4-dihydroxyphenylalanine methyl ester, amino(9)-1,2,3,4-tetrahydroacridine, lanatoside C, methotrexate, nalidixic acid, nystatin, pergolide, rifampicin, tetracycline, vitamin A, acebutolol, amikacin sulfate, amiodarone, amitriptyline, amoxicilin, amphotericin B, ampicilin trihydrate, aminone, aztreonam, beclomethasone, benzydamine, benztropine, bromo(2)-alpha-ergocryptine, buspirone, carbamazepine, beta-carbamylmethylcholine, carbenicillin, cefmetazole, cefoperazone, cefotaxime, ceftriaxone, cefuroxime, cephalothin, cephradine, chlorambucil, chlorothiazide, chlorprothixene, chlorthalidone, clofibrate, cimetidine, ciprofibrate, ciprofloxacin, clonidine, clopamide, cloxacillin, colistin, cyproterone acetate, cytosine beta-D-arabinofuranoside, dacarbazine, desipramine, dexamethasone, dicloxacillin, dihydrotachysterol, dobutamine, doxycycline, droperidol, enoxacin, epinephrine, ergocalciferol, ethionamde, flecainide, flunarizine, fusidic acid, glibenclamide, hydroxyurea, isoetharine, ivermectin, lansoprazole, lincomycin, hydroxychloroquine sulfate, mebeverine, meclizine, methoxamine hydrochloride, methyl(8-)-N-vanillyl-6-nonenamide, metronidazole, mexiletine and mianserin.

Compounds that showed S100A4 activity are shown in Table 1, with their $IC_{50}$ measurement.

TABLE 1

| Additive | Arbitrary Fluorescence Units | $IC_{50}$ (μM) |
|---|---|---|
| no addition | 8475 | — |
| calcium | 14996 | — |
| calcium + EGTA | 6088 | — |
| flupenthixol-cis | 6449 | 59 |
| fluphenazine | 6908 | 46 |
| perphenazine | 7399 | 164 |
| prochlorperazine | 5505 | 33 |
| trifluoperazine | 7939 | 34 |

TABLE 1-continued

| Additive | Arbitrary Fluorescence Units | IC$_{50}$ (µM) |
|---|---|---|
| chlorprothixene | 7977 | 145 |
| cyproheptadine | 8122 | 256 |
| clomipramine | 7898 | 133 |
| bepridil | 6954 | 35 |
| ketoconazole | 7759 | 23 |
| loperamide | 3820 | 18 |

These S100A4 inhibitors are useful for metastatic cancer treatment as well as being lead compounds to identify more potent S100A4 inhibitors.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of determining whether a compound is an inhibitor of Ca$^{2+}$ binding activation of a human S100 protein, the method comprising combining the compound with Ca$^{2+}$ and a biosensor of the S100 protein in an aqueous solution,
wherein the biosensor comprises a human S100 protein that has a fluorescent dye covalently bound at an amino acid residue thereof which is at a three-dimensional position equivalent to Cys81 of S100A4, wherein upon the binding of Ca$^{2+}$ to the biosensor of the S100 protein the fluorescence of the fluorescent dye increases,
wherein the compound is determined to be an inhibitor of Ca$^{2+}$ binding activation of the human S100 protein if the compound prevents increased fluorescence of the fluorescent dye upon exposure of the biosensor of the S100 protein to the Ca$^{2+}$.

2. The method of claim 1, wherein the human S100 protein is S100A1, S100A2, S100A3, S100A4, S100A5, S100A6, S100A7, S100A7L2, S100A7L3, S100A7L4, S100A8, S100A9, S100A10, S100A11, S100A12, S100A13, S100A14, S100A15, S100A16, S100B, S100P, S100Z or CALB3.

3. The method of claim 1, wherein the human S100 protein is S100A4.

4. The method of claim 1, wherein the dye is a merocyanine dye.

5. The method of claim 1, wherein the fluorescence of the biosensor in the presence of the compound is measured both before and after adding Ca$^{2+}$.

6. The method of claim 1, further comprising determining whether the compound inhibits the interaction of the S100 protein with a target of the S100 protein.

7. The method of claim 1, wherein the compound is part of a chemical library, wherein at least 10 compounds of the chemical library are tested for the ability to inhibit an S100 protein.

8. The method of claim 7, wherein at least 50 compounds of the chemical library are tested for the ability to inhibit an S100 protein.

9. The method of claim 7, wherein at least 100 compounds of the chemical library are tested for the ability to inhibit an S100 protein.

10. The method of claim 1, wherein the compound is a modification of a known S100 inhibitor, wherein the modification changes less than half of the known S100 inhibitor, by weight.

11. The method of claim 10, wherein the modification changes one moiety of the known S100 inhibitor.

12. The method of claim 10, wherein the known S100 inhibitor is an S100A4 inhibitor.

13. The method of claim 12, wherein the S100A4 inhibitor is flupenthixol-cis, fluphenazine, perphenazine, prochlorperazine, trifluoperazine, chlorprothixene, cyproheptadine, clomipramine, bepridil, ketoconazole, or loperamine.

* * * * *